US011357949B2

(12) United States Patent
Belson

(10) Patent No.: US 11,357,949 B2
(45) Date of Patent: Jun. 14, 2022

(54) TEMPERATURE MEASUREMENT AND FEEDBACK FOR THERAPEUTIC HYPOTHERMIA

(71) Applicant: Qool Therapeutics, Inc., Menlo Park, CA (US)

(72) Inventor: Amir Belson, Savyon (IL)

(73) Assignee: Pagonia Medical, Inc., Menlo Park, CA (US)

( * ) Notice: Subject to any disclaimer, the term of this patent is extended or adjusted under 35 U.S.C. 154(b) by 690 days.

(21) Appl. No.: 16/273,941

(22) Filed: Feb. 12, 2019

(65) Prior Publication Data

US 2019/0175866 A1 Jun. 13, 2019

Related U.S. Application Data

(63) Continuation of application No. 14/479,128, filed on Sep. 5, 2014, now Pat. No. 10,238,831.
(Continued)

(51) Int. Cl.
*A61M 19/00* (2006.01)
*A61M 16/04* (2006.01)
(Continued)

(52) U.S. Cl.
CPC ........ *A61M 19/00* (2013.01); *A61M 16/0051* (2013.01); *A61M 16/026* (2017.08);
(Continued)

(58) Field of Classification Search
CPC ......... A61B 5/01; A61B 5/4836; A61B 5/486; A61F 2007/0006; A61F 2007/0009; A61F 2007/001; A61F 2007/0017; A61F 2007/0018; A61F 2007/0022; A61F 2007/006; A61F 2007/0061; A61F 2007/0063; A61F 2007/0064;
(Continued)

(56) References Cited

U.S. PATENT DOCUMENTS 2,687,623 A 8/1954 Aubrey
4,046,139 A 9/1977 Horn et al.
(Continued)

FOREIGN PATENT DOCUMENTS

CN 102271741 A 12/2011
DE 29909141 U1 9/1999
(Continued)

OTHER PUBLICATIONS

"EESR for EP18181995 dated Oct. 25, 2018".
(Continued)

*Primary Examiner* — Annette Dixon
(74) *Attorney, Agent, or Firm* — Wilson Sonsini Goodrich & Rosati

(57) ABSTRACT

A treatment system includes a delivery device which delivers a combination of a breathing gas and frozen ice or other particles to a patient in order to induce hypothermia. The treatment system also includes a temperature system for measuring the temperature of exhaled gases and a controller which can adjust the duration or rate at which the ice particles are delivered in order to control the patient's core temperature based on the measured exhalation gas temperature.

10 Claims, 3 Drawing Sheets

Related U.S. Application Data

(60) Provisional application No. 61/875,093, filed on Sep. 8, 2013.

(51) Int. Cl.
  *A61M 16/00* (2006.01)
  *A61M 16/06* (2006.01)
  *A61M 16/10* (2006.01)
  *A61M 16/20* (2006.01)
  *A61M 5/44* (2006.01)
  *A61F 7/12* (2006.01)

(52) U.S. Cl.
  CPC ........ *A61M 16/06* (2013.01); *A61M 16/1075* (2013.01); *A61F 7/12* (2013.01); *A61M 5/44* (2013.01); *A61M 16/0069* (2014.02); *A61M 16/04* (2013.01); *A61M 16/0486* (2014.02); *A61M 16/201* (2014.02); *A61M 2205/18* (2013.01); *A61M 2205/3368* (2013.01); *A61M 2205/3606* (2013.01); *A61M 2205/3646* (2013.01); *A61M 2230/50* (2013.01)

(58) Field of Classification Search
  CPC ...... A61F 2007/0068; A61F 2007/0091; A61F 2007/0093; A61F 2007/0095; A61F 2007/0292; A61F 2007/126; A61F 7/0085; A61F 7/10; A61F 7/12; A61M 11/00; A61M 11/001; A61M 11/005; A61M 11/042; A61M 11/06; A61M 11/065; A61M 15/00; A61M 15/0065; A61M 15/0085; A61M 15/0086; A61M 15/009; A61M 16/0051; A61M 16/0069; A61M 16/01; A61M 16/024; A61M 16/026; A61M 16/04; A61M 16/0404; A61M 16/0409; A61M 16/042; A61M 16/0431; A61M 16/0434; A61M 16/0486; A61M 16/0488; A61M 16/06; A61M 16/0666; A61M 16/0677; A61M 16/08; A61M 16/0816; A61M 16/0833; A61M 16/0866; A61M 16/0875; A61M 16/10; A61M 16/1075; A61M 16/1095; A61M 16/12; A61M 16/14; A61M 16/16; A61M 16/201; A61M 16/202; A61M 16/204; A61M 16/208; A61M 19/00; A61M 2016/0021; A61M 2016/0024; A61M 2016/0027; A61M 2039/244; A61M 2039/248; A61M 2202/0007; A61M 2202/0208; A61M 2202/0225; A61M 2202/025; A61M 2202/0275; A61M 2202/03; A61M 2202/06; A61M 2205/18; A61M 2205/3331; A61M 2205/3344; A61M 2205/3368; A61M 2205/3606; A61M 2205/362; A61M 2205/3633; A61M 2205/3646; A61M 2205/3653; A61M 2205/366; A61M 2205/3673; A61M 2206/16; A61M 2230/005; A61M 2230/50; A61M 39/24; A61M 5/44; A61P 25/08
  See application file for complete search history.

(56) References Cited

U.S. PATENT DOCUMENTS

| | | | |
|---|---|---|---|
| 4,711,375 | A | 12/1987 | Maeder et al. |
| 5,035,750 | A | 7/1991 | Tada et al. |
| 5,203,794 | A | 4/1993 | Stratford et al. |
| 5,474,533 | A | 12/1995 | Ward et al. |
| 5,755,756 | A | 5/1998 | Freedman, Jr. et al. |
| 5,964,217 | A | 10/1999 | Christopher |
| 6,014,972 | A * | 1/2000 | Sladek ............... A61M 15/0065 128/203.12 |
| 6,089,229 | A * | 7/2000 | Bathe ................. A61M 16/0677 128/204.21 |
| 6,149,624 | A | 11/2000 | McShane |
| 6,244,052 | B1 | 6/2001 | Kasza |
| 6,303,156 | B1 | 10/2001 | Ferrigno |
| 6,306,119 | B1 | 10/2001 | Weber et al. |
| 6,547,811 | B1 | 4/2003 | Becker et al. |
| 6,555,057 | B1 | 4/2003 | Barbut et al. |
| 6,572,638 | B1 | 6/2003 | Dae et al. |
| 6,582,457 | B2 | 6/2003 | Dae et al. |
| 6,585,752 | B2 | 7/2003 | Dobak et al. |
| 6,669,661 | B1 | 12/2003 | Yee |
| 6,736,790 | B2 | 5/2004 | Barbut et al. |
| 6,962,601 | B2 | 11/2005 | Becker et al. |
| 6,983,749 | B2 | 1/2006 | Kumar et al. |
| 7,070,612 | B1 | 7/2006 | Collins et al. |
| 7,422,601 | B2 | 9/2008 | Becker et al. |
| 7,892,269 | B2 | 2/2011 | Collins et al. |
| 8,100,123 | B2 * | 1/2012 | Belson ................. A61B 5/4836 128/204.15 |
| 8,281,786 | B2 | 10/2012 | Belson |
| 8,308,787 | B2 | 11/2012 | Kreck |
| 8,402,968 | B2 | 3/2013 | Belson |
| 8,465,535 | B2 | 6/2013 | Harris et al. |
| 9,004,066 | B2 | 4/2015 | Belson |
| 9,320,644 | B2 | 4/2016 | Kreck et al. |
| 9,414,959 | B2 | 8/2016 | Belson et al. |
| 9,522,080 | B2 | 12/2016 | Collins et al. |
| 9,757,272 | B2 | 9/2017 | Belson et al. |
| 10,238,831 | B2 * | 3/2019 | Belson ................. A61M 16/06 |
| 10,893,976 | B2 * | 1/2021 | Belson ................. A61M 11/001 |
| 11,020,269 | B2 * | 6/2021 | Mirizzi ................. A61M 16/14 |
| 2002/0023640 | A1 | 2/2002 | Nightengale |
| 2003/0024530 | A1 | 2/2003 | Sniadach |
| 2003/0056789 | A1 | 3/2003 | Takano et al. |
| 2003/0066304 | A1 | 4/2003 | Becker et al. |
| 2003/0131844 | A1 | 7/2003 | Kumar et al. |
| 2003/0136402 | A1 | 7/2003 | Jiang et al. |
| 2003/0152500 | A1 | 8/2003 | Dalziel et al. |
| 2004/0064171 | A1 | 4/2004 | Briscoe et al. |
| 2004/0092920 | A1 | 5/2004 | Rozenshpeer |
| 2004/0138608 | A1 | 7/2004 | Barbut et al. |
| 2004/0158303 | A1 | 8/2004 | Lennox et al. |
| 2004/0210281 | A1 | 10/2004 | Dzeng et al. |
| 2004/0261438 | A1 | 12/2004 | Clulow et al. |
| 2005/0042170 | A1 | 2/2005 | Jiang et al. |
| 2005/0177212 | A1 | 8/2005 | Njemanze et al. |
| 2005/0279108 | A1 | 12/2005 | Akselband et al. |
| 2006/0036302 | A1 | 2/2006 | Kasza et al. |
| 2006/0190066 | A1 | 8/2006 | Worthen |
| 2006/0276552 | A1 | 12/2006 | Barbut et al. |
| 2007/0123813 | A1 | 5/2007 | Barbut et al. |
| 2008/0015543 | A1 | 1/2008 | Wang |
| 2008/0262377 | A1 | 10/2008 | Belson |
| 2009/0076573 | A1 | 3/2009 | Burnett et al. |
| 2009/0107491 | A1 | 4/2009 | Belson |
| 2009/0125087 | A1 | 5/2009 | Becker et al. |
| 2009/0192505 | A1 | 7/2009 | Askew et al. |
| 2010/0324635 | A1 | 12/2010 | Kreck |
| 2011/0005522 | A1 | 1/2011 | Vervoort |
| 2012/0031405 | A1 * | 2/2012 | Geist ..................... A61F 7/0085 128/204.15 |
| 2012/0080031 | A1 | 4/2012 | Belson |
| 2012/0167878 | A1 * | 7/2012 | Belson ................. A61M 19/00 128/200.16 |
| 2012/0310312 | A1 | 12/2012 | Yee |
| 2013/0000642 | A1 | 1/2013 | Fearnot et al. |
| 2013/0085554 | A1 | 4/2013 | Belson et al. |
| 2013/0116761 | A1 | 5/2013 | Kreck |
| 2013/0204331 | A1 | 8/2013 | Harikrishna et al. |
| 2013/0226077 | A1 | 8/2013 | Burnett et al. |
| 2014/0060534 | A1 | 3/2014 | Belson |

(56) References Cited

U.S. PATENT DOCUMENTS

| | | | |
|---|---|---|---|
| 2014/0350648 A1* | 11/2014 | Ericson | A61F 7/10 |
| | | | 607/105 |
| 2015/0151073 A1 | 6/2015 | Shushunov | |
| 2015/0351955 A1 | 12/2015 | Belson | |
| 2016/0175141 A1 | 6/2016 | Wu et al. | |
| 2016/0296365 A1 | 10/2016 | Kreck et al. | |
| 2016/0324685 A1 | 11/2016 | Belson | |
| 2017/0049618 A1 | 2/2017 | Ward et al. | |
| 2017/0112662 A1 | 4/2017 | Collins et al. | |
| 2017/0266037 A1 | 9/2017 | Belson | |
| 2018/0153739 A1 | 6/2018 | Mirizzi et al. | |
| 2021/0137731 A1* | 5/2021 | Mirizzi | A61M 16/0875 |

FOREIGN PATENT DOCUMENTS

| | | |
|---|---|---|
| DE | 102007019616 A1 | 10/2008 |
| EP | 0206982 A1 | 12/1986 |
| JP | H01203700 A | 8/1989 |
| JP | 2003505190 A | 2/2003 |
| JP | 2007518544 A | 7/2007 |
| WO | WO-9966938 A1 | 12/1999 |
| WO | WO-0018459 A1 | 4/2000 |
| WO | WO-0108593 A2 | 2/2001 |
| WO | WO-0109558 A1 | 2/2001 |
| WO | WO-02085417 A2 | 10/2002 |
| WO | WO-03047603 A2 | 6/2003 |
| WO | WO-03059425 A1 | 7/2003 |
| WO | WO-03047603 A3 | 10/2003 |
| WO | WO-02085417 A3 | 12/2003 |
| WO | WO-2005070035 A2 | 8/2005 |
| WO | WO-2005070035 A3 | 12/2005 |
| WO | WO-2005113046 A2 | 12/2005 |
| WO | WO-2005113046 A3 | 3/2007 |
| WO | WO-2009009540 A1 | 1/2009 |
| WO | WO-2009035596 A4 | 4/2009 |
| WO | WO-2010065616 A1 | 6/2010 |
| WO | WO-2010090509 A1 | 8/2010 |
| WO | WO-2013036540 A1 | 3/2013 |
| WO | WO-2013090730 A1 | 6/2013 |
| WO | WO-2015035315 A2 | 3/2015 |
| WO | WO-2015035315 A3 | 5/2015 |
| WO | WO-2016138045 A1 | 9/2016 |

OTHER PUBLICATIONS

European search report and opinion dated Oct. 13, 2010 for EP Application No. EP 05712159.2.
European search report and search opinion dated Jun. 1, 2012 for EP Application No. 09831036.0.
European Search Report dated May 11, 2017 for EP Application No. 14842468.2.
"International search report and written opinion dated Apr. 2, 2015 for PCT/US2014/054579."
International search report and written opinion dated May 6, 2016 for PCT/US2016/019202.
International search report dated May 3, 2010 for PCT/US2009/066380.
International search report dated Sep. 8, 2005 for PCT/US2005/002600.
Notice of allowance dated Jan. 21, 2015 for U.S. Appl. No. 13/780,866.
Notice of Allowance dated Apr. 11, 2017 for U.S. Appl. No. 14/657,408.
Notice of allowance dated Jul. 23, 2012 for U.S. Appl. No. 12/269,009.
Notice of Allowance dated Aug. 23, 2017 for U.S. Appl. No. 14/479,128.
Notice of allowance dated Oct. 31, 2011 for U.S. Appl. No. 10/587,103.
Notice of allowance dated Nov. 23, 2012 for U.S. Appl. No. 13/326,101.
Office Action dated Mar. 17, 2017 for U.S. Appl. No. 14/479,128.
Office Action dated Mar. 26, 2015 for U.S. Appl. No. 13/255,867.
Office action dated Apr. 10, 2012 for U.S. Appl. No. 13/326,101.
Office Action dated May 30, 2017 for U.S. Appl. No. 13/255,867.
Office action dated Jul. 3, 2014 for U.S. Appl. No. 13/780,866.
Office Action dated Aug. 11, 2016 for U.S. Appl. No. 13/255,867.
Office action dated Sep. 14, 2012 for U.S. Appl. No. 13/326,101.
Office Action dated Sep. 15, 2016 for U.S. Appl. No. 14/657,408.
Office Action dated Sep. 17, 2015 for U.S. Appl. No. 13/255,867.
Office Action dated Oct. 11, 2016 for U.S. Appl. No. 14/479,128.
Office Action dated Sep. 15, 2017 for U.S. Appl. No. 14/479,128.
POGONIP in Pittsburg air. Weather man there says it's death from frozen fog. New York Times. Jan. 12, 1910.
U.S. Appl. No. 14/479,128 Office Action dated May 15, 2018.
Office action dated Mar. 3, 2020 for U.S. Appl. No. 15/575,306.
Office action dated Mar. 9, 2020 for U.S. Appl. No. 15/610,291.

* cited by examiner

TEMPERATURE MEASUREMENT AND FEEDBACK FOR THERAPEUTIC HYPOTHERMIA

CROSS-REFERENCE TO RELATED APPLICATIONS

This application is a continuation of U.S. patent application Ser. No. 14/479,128, filed Sep. 5, 2014, which claims the benefit of U.S. Provisional Application Ser. No. 61/875,093, filed Sep. 8, 2013, the entire content of which is incorporated herein by reference.

BACKGROUND OF THE INVENTION

1. Field of the Invention

The present invention relates generally to systems and methods for heat exchange with a patient's airways and lungs for selective modification and control of a patient's body temperature. More particularly, it relates to a system and a method for controlling a patient's core body temperature by introducing frozen particles into the patient's respiratory system while monitoring exhalation temperature.

Normal functioning of the human animal requires a body temperature of approximately 37 degrees Celsius (98.6 degrees Fahrenheit). The body can self-compensate for small upward or downward variations in temperature through the activation of a built-in thermoregulatory system, controlled by temperature sensors in the skin. The response to an upward variation in body temperature is the initiation of perspiration, which moves moisture from body tissues to the body surface. When the moisture reaches the surface it evaporates, carrying with it a quantity of heat. The response to a downward variation in body temperature is shivering, which is the body's attempt to generate heat. Shivering is an involuntary contraction and expansion of muscle tissue occurring on a large scale. This muscle action creates heat through friction.

Hypothermia is defined as a core temperature of less than 35° C. and is considered a clinical state of subnormal temperature when the body is unable to generate sufficient heat to effectively maintain functions. Many variables contribute to the development of hypothermia. Age, health, nutrition, body size, exhaustion, exposure, duration of exposure, wind, temperature, wetness, medication and intoxicants may decrease heat production, increase heat loss, or interfere with thermostability. The healthy individual's compensatory responses to heat loss via conduction, convection, radiation, evaporation and respiration may be overwhelmed by exposure. Medications may interfere with thermoregulation. Acute or chronic central nervous system processes may decrease the effectiveness of thermoregulation.

Recent medical reports have described the use of controlled hypothermia as a means to reduce oxygen consumption of tissue, such as the heart muscle and the brain during decreased perfusion that occurs as a result of myocardial infarction and ischemic stroke (respectively), which leads to reduced damage and decrease of the infarcted area. Medical reports have also described the prophylactic use of controlled hypothermia during cardiac surgery or interventional cardiology procedures for reducing damage from ischemia and/or embolization in the heart and brain during and after the procedure.

U.S. Pat. Nos. 8,100,123; 8,281,786; 8,402,968; and U.S. Patent Publ. No. 2013/0085554, all commonly assigned with the present application and incorporated herein by reference, describe improved systems and methods for inducing hypothermia in patients by introducing ice or other frozen particles into the lungs or other body cavities of the patient. As the frozen particles melt, heat is absorbed by the heat (enthalpy) of melting, and the body of the patient is cooled. While offering considerable advantages of prior systems for inducing hypothermia, the respiratory introduction of ice and other frozen particles can be difficult to control and has the potential to cool a patient beyond any desired therapeutic range.

For those reasons, it would be desirable to provide methods and systems for inducing hypothermia with a reduced risk of overcooling the patient. Such methods and systems should further provide for rapid attainment of a desired core body temperature and subsequent maintenance of the core temperature with minimum deviation. At least some of these objections will be met by the inventions described below.

2. Description of the Background Art

U.S. Pat. Nos. 8,100,123; 8,281,786; 8,402,968; and U.S. Patent Publ. No. 2013/0085554 have been described above. U.S. Patent Publ. 2013/0226077 describes monitoring exhalation temperature in a peritoneal hypothermia system that optionally delivers phase change fluids to the peritoneal cavity.

SUMMARY OF THE INVENTION

In a first aspect, the present invention provides a method for lowering a core body temperature of a patient. The method comprises delivering a breathing gas to a respiratory system of the patient during a series of inhalation cycles. The respiratory system includes the lungs, the trachea, the nasal sinuses and nasal passages. In addition to the breathing gas, frozen particles are also delivered to the respiratory system during at least a portion of some of the inhalation cycles. The particles are usually ice, comprising mostly or entirely water or saline, but could also be frozen carbon dioxide or other non-toxic materials which can melt or sublimate to absorb body heat as a result of an enthalpy of melting or sublimation. The temperature of exhaled gases is measured during at least some exhalation cycles, and the amount of frozen particles delivered to the patient can be adjusted in order to achieve a target core temperature based on the measured temperature of the exhalation gases.

The breathing gas and the frozen particles can be delivered in a variety of ways including using a breathing mask as taught in U.S. Pat. Nos. 8,100,123; 8,281,786; and 8,402,968, the full disclosures of which are incorporated herein by reference. In other embodiments, the breathing gas and/or the frozen particles may be delivered through an endotracheal tube. The breathing gas and the frozen particles can be delivered through the same conduits or through separate conduits, and the frozen particles can be generated externally of the delivery system and/or in situ within the delivery system.

Adjusting the amount of frozen particles being delivered (which determines the cooling capacity of the system) may comprise adjusting a duration and/or a rate of the frozen particle delivery during individual inhalations. The method will typically comprise at least an initial phase wherein a sufficient amount of the frozen particles is delivered to rapidly lower the core body temperature to a target core temperature, generally in a target range from 33° C. to 35° C., and a maintenance phase wherein a lesser amount of frozen particles and/or other cooling media is delivered to maintain the target core temperature in the desired target range without lowering the patient's core temperature beyond a desired lower threshold.

In a second aspect, the present invention provides a system for lowering a core body temperature of a patient. The system comprises at least one conduit configured to deliver a an amount of frozen particles (typically together with a breathing gas) to the patient's respiratory system. A temperature sensor is configured to measure a temperature of gas being exhaled through the at least one conduit, and a controller is configured to display exhalation temperature and optionally to adjust the amount, duration and/or rate of delivery of frozen particles through the at least one conduit. Using the system, a target core temperature of the patient can be achieved and maintained by manually and/or automatically adjusting the amount or rate of frozen particles delivered to the respiratory system of the patient.

In specific embodiments, the system includes one conduit for delivering the breathing gas and a separate conduit for delivering the frozen particles, where the one breathing gas conduit usually also provides an exhalation path. In particular embodiments, the conduit may comprise a breathing mask or an endotracheal and/or intranasal tube.

The controller may be configured to automatically control the delivery amount or rate of frozen particles in response to the exhalation temperature measured by the temperature sensor according to a feedback algorithm. In other embodiments, the controller may be configured to allow a user to manually control the delivery amount or rate of frozen particles in response to the exhalation temperature measured by the temperature sensor.

The system may optionally include an audible or visual alarm configured to detect any one of a variety of abnormal conditions, particularly including a reduction in the exhalation and/or the body core temperature below a lower safety threshold. Conveniently, the exhalation temperature sensor can be used for that function as well as for control. Other sensors that measure lung fluid (such as thoracic impedance sensors), humidity sensors in the breathing tube that measure the presence of fluid in the exhaled air, protein detectors that measure the present of proteins in the exhalation tube (protein as a marker for pulmonary edema), blood sensors for detecting the presence of blood in the fluid in the exhalation tube (another marker of pulmonary edema), and the like. The system may also provide for the automatic reduction or cessation of frozen particle deliver to the lungs whenever an alarm condition is detected.

BRIEF DESCRIPTION OF THE DRAWINGS

The invention will be described, by way of example, and with reference to the accompanying diagrammatic drawings, in which.

DETAILED DESCRIPTION OF THE INVENTION

Figure 1:
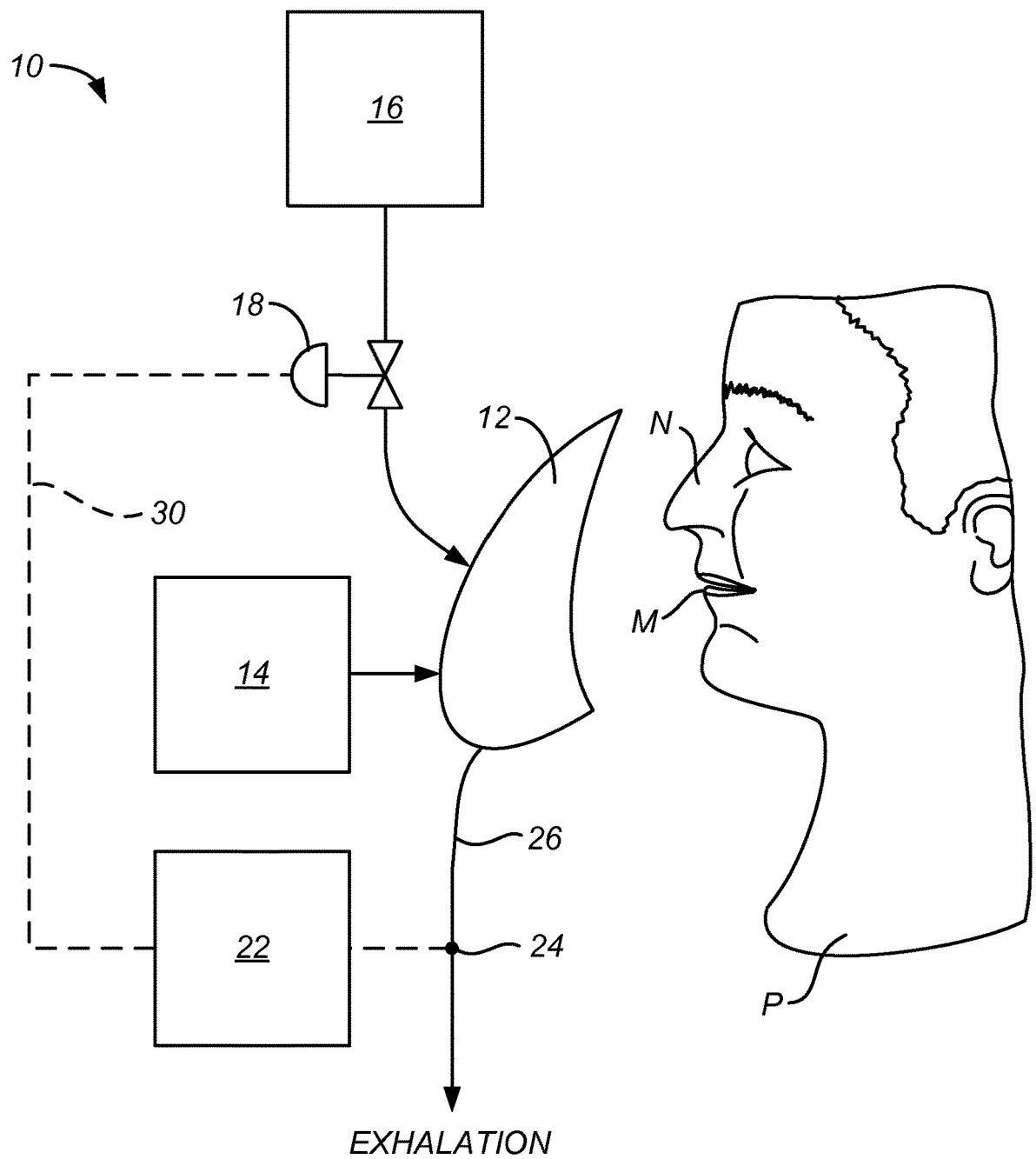
FIG. 1 illustrates a diagram of a system comprising a breathing mask for delivering a frozen mist of frozen particles to a patient using the systems of the present invention.

The methods and systems of the present invention induce hypothermia in a patient by introducing ice or other non-toxic, biologically compatible frozen particles into a patient's lungs or other regions of the respiratory system. Melting or sublimation of the frozen particles provides a high rate of enthalpic heat absorption which rapidly cools the lungs and other regions of the respiratory tract, thus cooling the blood in the lungs which in turn flows to cool the heart and brain as well as the body core and extremities as cooled blood is circulated through the patient.

The present invention provides methods for monitoring the patient's core body temperature, particularly including the temperature of the lungs and heart, by measuring the temperature of the patient's exhalation to provide a real time profile of the body core temperature. The temperature of the exhaled air is measured during at least a portion of at least some of the exhalation cycles and the temperature profile, typically being measured during the entire duration of each exhalation cycle in order to determine a lowest exhaled air temperature (during that exhalation cycle) which is recorded and stored. The temperature of the exhaled air, and in particular the lowest temperature of the air exhaled in any exhalation cycle, closely correlates with the body core temperature, optionally after a calibration phase, particularly with the lung and heart temperatures at the time of exhalation. Such accurate, real time body core temperature measurement allows for control of the body core temperature, for example by controlling the amount of frozen particles which are delivered to the patient's respiratory at any given time.

The system may optionally include an automatic controller or other programmable component which allows control of the body core temperature based upon the measured exhalation temperature using conventional control algorithms, such as proportional control, derivative control, combinations of proportional and derivative control, as well as feed forward control algorithms which rely on modeling the heat transfer and other characteristics which are related to the correlation between exhaled air temperature and body core temperature. The algorithm can optionally generate an alarm when a temperature exceeds or falls lower than the pre-determined target range. Alternatively, the control can be done manually where a physician or other user is able to adjust the amount or rate of the delivery of ice particles to the patient to achieve rapid cooling to a target core temperature.

Once the target core temperature is reached, the methods of the systems of the present invention will further allow for maintenance of that temperature. For example, the system or doctor may reduce the amount of frozen particles being delivered to the patient to an amount sufficient to maintain but not further lower the body core temperature. Alternatively, other cooling fluids may be utilized in addition to or in place of the frozen particles. Still further alternatively, the use of cooling jackets and other patient cooling apparatus may be used in place of or in addition to the respiratory cooling systems once the target core temperature has been reached.

The system may also include sensors to detect early signs of pulmonary edema or lungs fluid overload which will enable lowering the ice amount being delivered. The controller could also be connected to receive data from the ventilator data and be programed to automatically or manually (by alarming) reduce the ice dose if the ventilator show signs of increased lung resistance to the ventilation.

Referring now to FIG. 1, a first exemplary system 10 constructed in accordance with the principles of the present invention for inducing hypothermia in a patient P will be described. The first system 10 uses a breathing mask 12 to deliver both a breathing gas, typically air or oxygen, and the frozen particles, typically frozen saline particles, to the patient. The breathing mask which covers a patient's mouth M and nose N is connected directly to a source of breathing gas 14 which will provide the gas to the patient P in a manner conventional for breathing masks. In addition, a source of frozen particles 16 will be connected to the breathing mask 12 through a valve 18 which may be either a control valve to vary the amount of ice being delivered or which may be an on-off valve, such as a solenoid. The manner in which the ice or other frozen particles are delivered to the breathing mask may generally be as taught in any of the prior references incorporated hereinabove.

A controller 22 is connected to a temperature sensor 24 present in an output line or port 26 which carries the exhaled breath from the patient. The temperature sensor, of course, may be disposed within the breathing mask and preferably will be as close to the patient's mouth M as possible in order to measure the exhaled gas temperature as accurately as possible. The controller 22 will measure the temperature from the sensor 24 and will typically include an output display which is visible to the user. The user may thus manually control the control valve 18 in order to adjust the flow of the frozen particles or the timing of the flow. In other embodiments, however, the controller 22 will provide a control signal via line 30 to the valve 18 in order to automatically control the valve, including both on-off control as well as proportional control, integral control, proportional-integral control and other conventional or unconventional control algorithms.

The system may optionally have the ability to synchronize the frozen particle delivery to a specific phase of breathing, preferably the inhalation phase or cycle or a specific portion of the inhalation phase or cycle. The breathing phase and stage could be tracked using an exhaled gas sensor and/or a sensor on the patient's chest or other part of the patient's upper body that will send chest expansion which represents inhalation and chest volume reduction as part of exhalation. In addition to the mask, the system may include an additional tube which will be in continuation with the frozen particle delivery tube and potentially also of the breathing air tube. This extension tube will be positioned deeper in the pharynx but still external to the vocal cords. The purpose is to reduce the heat exposure of the ice to the buccal membrane and the rest of the mouth.

Figure 2:
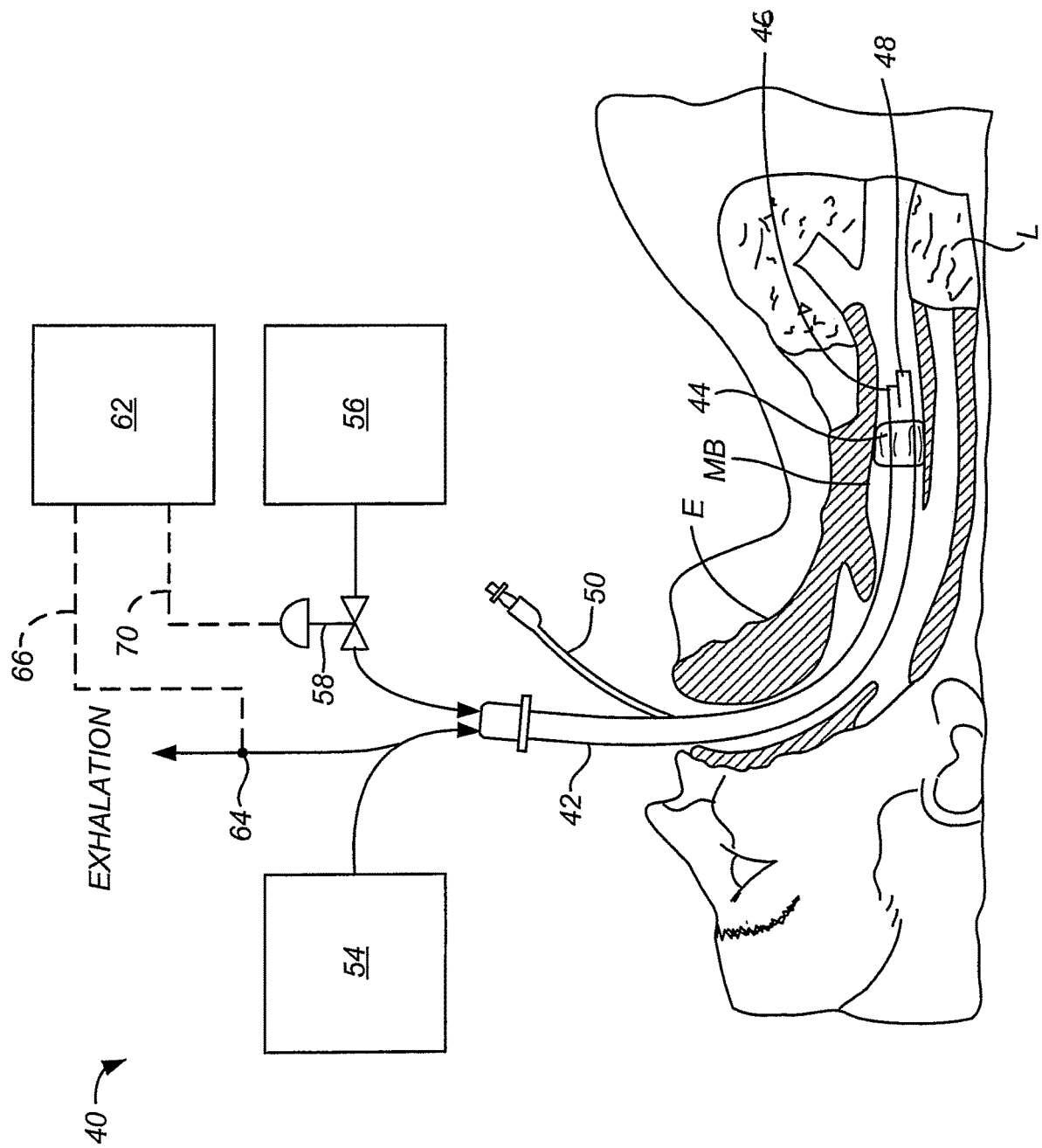
FIG. 2 illustrates a diagram of a system comprising an endotracheal tube for delivery a frozen mist of frozen particles to a patient.

A second exemplary system 40 constructed in accordance with the principles of the present invention is illustrated in FIG. 2. The system of FIG. 2 is similar to that of FIG. 1 but employs an endotracheal tube and/or breathing conduits 42 which deliver the breathing gas and the frozen particles directly to the patient's P lungs L. Typically, the conduit(s) or endotracheal tube will include a cuff 44 which can be inflated via an inflation tube 50 to isolate a distal end of the conduit or endotracheal tube within a main bronchus MB of the patient in a manner conventional for endotracheal tubes. The endotracheal tube or conduits 42 will have at least two lumens terminating in separate distal ports 46 and 48 to separately deliver the breathing gas and the frozen particles to the patient's lungs L. The distal ports 46 and 48 will typically be axially or otherwise separated so that the frozen particles do not clog the breathing lumen and the exhaled gas temperature will not be directly affected by the particles. Usually, the breathing gas port will be disposed upstream (toward the mouth M) in the main bronchus MB to minimize any direct contamination. Also, as will be described below, the frozen particles are preferably delivered only during the patient's inhalation cycle so the risk of ice entering the exhalation lumen during the patient's exhalation cycle is reduced.

After the patient P has been intubated with the conduit(s) or endotracheal tube 42, breathing air will be provided in a conventional manner from a breathing source 54. In addition, frozen particles will be delivered from a source of frozen particles 56 through a valve 58. A controller 62 senses the temperature of the patient's exhalation through a temperature sensor 64 connected to the controller by line 66. The temperature sensor 64 is located at an outlet of the conduit or endotracheal tube 42. It will be appreciated that the sensor could be located nearer a distal end of the conduit or endotracheal tube so that the temperature being measured is closer to the lungs. As with the first system, the temperature measured by the sensor 64 will typically be displayed on the controller 62 allowing a physician or other user to manually adjust the delivery of the ice particles in order to control the patient's core body temperature. Alternatively, valve 58 may be controlled via a signal line 70 which receives an automatic control signal from the controller 62 as described above with reference to the first system. The system may include other sensors, as described above, to indicate increased fluid in the lungs and/or increased ventilation pressure, and the data from those sensors may optionally be delivered to the controller to automatically reduce an amount of frozen particles delivered if needed.

Figure 3:
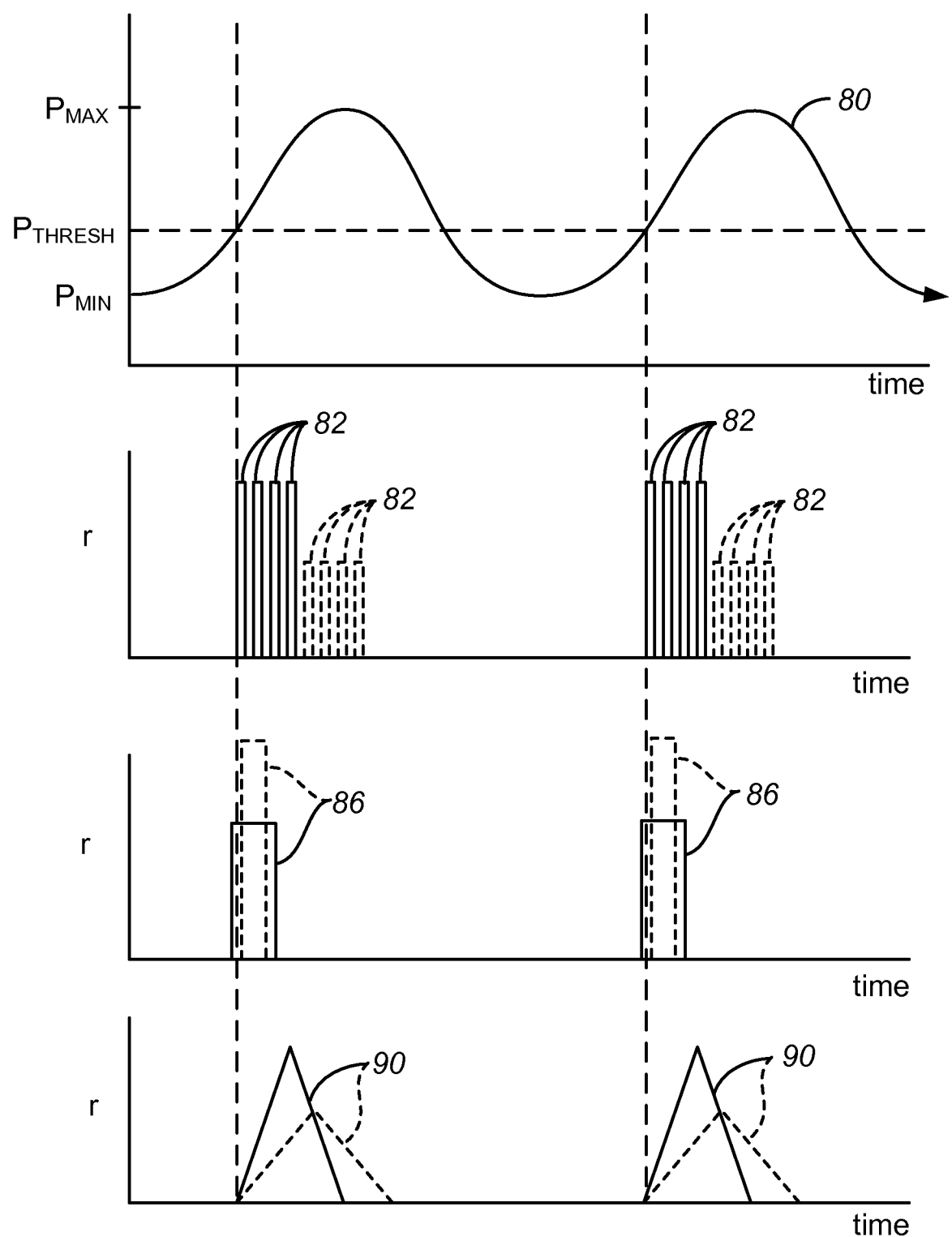
FIG. 3 is a graph illustrating exemplary frozen particle delivery patterns useful in the systems and methods of the present invention.

Referring now to FIG. 3, various protocols for delivering the frozen particles to the patient will be described. At its top, FIG. 3 illustrates a breathing pattern which may be induced by the breathing apparatus of the present invention. Breathing will follow a generally sinusoidal pressure pattern 80 where an inhalation cycle begins at a minimum value of pressure $P_{min}$ and terminates at a maximum pressure $P_{max}$. Once the $P_{max}$ has been reached, the patient will begin an exhalation cycle until the pressure reaches $P_{min}$ when the cycles will repeat.

Usually, the ice will be delivered during only a portion of the inhalation cycle. For example, as shown in a second graph from the top of FIG. 3, the frozen particles may be delivered in a series of bursts or puffs 82 coming usually in the middle of the inhalation cycle. The number of bursts or puffs and amount of ice in each individual burst or puff may be varied and the greater the number and/or volume of each puff will, of course, translate into greater cooling of the patient.

While use of the puffs is desirable since it helps prevent clogging of the ice delivery components of the system it is not necessary. The frozen particles may be delivered in a single spike 86 where the amount of frozen particles in the spike may be varied by controlling either the duration or the rate of the spike as shown in solid line and broken line, respectively. Similarly, the burst need not be in the form of a square wave but could also have a time-varying profile 90 as shown at the bottom of FIG. 3. Again, the duration or rate of the delivery will determine the total amount of frozen particles delivered in any given spike or release.

What is claimed is:

1. A system for lowering a core body temperature of a patient, said system comprising:
   at least one conduit configured to deliver a breathing gas and an amount of frozen particles to a respiratory system of the patient, wherein the at least one conduit has a breathing gas lumen terminating in a distal port at a distal end of the breathing gas lumen near a distal end of the conduit and a frozen particle lumen terminating in a distal port at a distal end of the frozen particle lumen near a distal end of the conduit, wherein the distal port at the distal end of the breathing gas lumen is separate from the distal port at the distal end of the frozen particle lumen to and both distal ports are configured to separately deliver the breathing gas and the frozen particles to the patient's trachea when the conduit is placed in a trachea of the patient;

wherein the breathing gas lumen is configured for both delivery of a breathing gas to the patient and exhalation of the breathing gas by the patient;

a temperature sensor configured to measure a temperature of gas being exhaled through the breathing gas lumen;

a controller configured to adjust a duration or an amount of delivery of frozen particles through the frozen particle lumen during individual inhalation cycles in response to changes in the temperature of the exhaled gas, whereby a target core temperature of the patient can be achieved and maintained.

2. A system as in claim 1, wherein the controller is configured to deliver of a series of bursts or puffs of the frozen particles through the frozen particle lumen.

3. A system as in claim 1, wherein, the distal port of the breathing gas lumen is axially separated from the distal port of the frozen particle lumen, wherein both distal ports are on the exterior of the conduit.

4. A system as in claim 1, wherein the at least one conduit comprises an endotracheal tube.

5. A system as in claim 1, wherein the controller is configured to automatically control the duration or amount of delivery of frozen particles in response to the exhalation temperature measured by the temperature sensor according to a feedback algorithm.

6. A system as in claim 1, wherein the controller is configured to allow a user to manually control the duration or amount of delivery of frozen particles in response to the exhalation temperature measured by the temperature sensor.

7. A system as in claim 1, wherein the controller includes an alarm that provides an audible or visual signal when a system sensor detects an alarm condition.

8. A system as in claim 7, wherein the alarm condition is selected from the group consisting of exhalation temperature below a lower threshold level and lung edema.

9. A system as in claim 7, wherein the system sensor is selected from the group consisting of a lung fluid detector, an exhaled gas humidity detector, an exhaled gas blood detector, and an exhaled gas protein detector.

10. A system as in claim 7, wherein the controller is configured to reduce or stop the delivery of frozen particles if an alarm condition is detected.

* * * * *